(12) United States Patent
Cammilleri

(10) Patent No.: US 7,942,233 B2
(45) Date of Patent: May 17, 2011

(54) METHOD TO PERSONALIZE A STETHOSCOPE

(76) Inventor: Tommaso Cammilleri, Virginia Beach, VA (US)

( * ) Notice: Subject to any disclaimer, the term of this patent is extended or adjusted under 35 U.S.C. 154(b) by 0 days.

(21) Appl. No.: 12/592,223

(22) Filed: Nov. 20, 2009

(65) Prior Publication Data
US 2010/0122866 A1    May 20, 2010

Related U.S. Application Data

(60) Provisional application No. 61/199,671, filed on Nov. 20, 2008.

(51) Int. Cl.
*A61B 7/02* (2006.01)
(52) U.S. Cl. .................. 181/131; D24/134; 600/528
(58) Field of Classification Search .......... 181/131; D24/134; 600/528
See application file for complete search history.

(56) References Cited

U.S. PATENT DOCUMENTS

| | | | | |
|---|---|---|---|---|
| 5,920,038 | A * | 7/1999 | Foster | 181/131 |
| 6,847,720 | B2 * | 1/2005 | Tseng | 381/67 |
| 7,424,929 | B1 * | 9/2008 | Martinez | 181/131 |
| 2006/0201738 | A1 * | 9/2006 | Krysztof | 181/131 |
| 2008/0245602 | A1 * | 10/2008 | Nakamura | 181/131 |
| 2009/0242318 | A1 * | 10/2009 | Gross | 181/131 |
| 2010/0122866 | A1 * | 5/2010 | Cammilleri | 181/131 |

* cited by examiner

*Primary Examiner* — Forrest M Phillips
(74) *Attorney, Agent, or Firm* — Robert M.M. Seto

(57) ABSTRACT

A method for personalizing a stethoscope, wherein the personalization permanently identifies the owner of the stethoscope and also decorates the stethoscope. The personalization does not deter from the normal operation of the stethoscope, and allows for full sterilization of the stethoscope. The diaphragm of the stethoscope, includes an exterior side that is adapted to come into contact with the patient and, an interior side that is not exposed to the outside. A design selected by the owner is applied, in reverse, to the interior surface of the diaphragm. The design is preferably painted on the diaphragm in stages, or layers. Using the present reverse application technique, images painted on the right-half of the interior surface, appear on the left-half, when viewed from the exterior of the stethoscope. Further, in the present application technique, the foreground is painted on, or applied, first, and the background of the personalization is applied last.

19 Claims, 8 Drawing Sheets

METHOD TO PERSONALIZE A STETHOSCOPE

BACKGROUND OF THE INVENTION

The present invention was originally disclosed in U.S. provisional patent application Ser. No. 61/199,671 filed on Nov. 20, 2008, and priority is claimed to the provisional patent application.

The present invention relates generally to the field of identification of personal equipment and more specifically to a method for personalizing a stethoscope.

A stethoscope is an acoustic medical device for auscultation, or listening to the internal sounds of an animal body. It is often used to listen to heart sounds. It is also used to listen to intestines and blood flow in arteries and veins. Less commonly, "mechanic's stethoscopes" are used to listen to internal sounds made by machines, such as diagnosing a malfunctioning automobile engine by listening to the sounds of its internal parts. Stethoscopes can also be used to check scientific vacuum chambers for leaks, and for various other small-scale acoustic monitoring tasks.

Acoustic stethoscopes are the most commonly used stethoscopes. Acoustic stethoscopes operate on the transmission of sound from the chest piece, via air-filled hollow tubes, to the listener's ears. The chest piece usually consists of a diaphragm (plastic disc) and a housing that supports the diaphragm. When the diaphragm is placed on the patient, body sounds vibrate the diaphragm, creating acoustic pressure waves which travel up the tubing to the listener's ears. A nurse or doctor using a stethoscope can listen to the sounds of a patient's body to determine normal functioning and abnormalities.

Stethoscopes must be carefully manufactured to insure proper operation. This means using the right materials and following exact specifications to insure optimum sound transfer. Because of the care and detail that must be put into the production of stethoscopes, high quality stethoscopes can be very expensive. As with anything valuable, owners like to place their name on it, or identify it in some way, so that if lost, they can later positively identify it. In the past, doctors and nurses have added items like name tags, smiley face buttons, and little clip-on stuffed animals. While these personalization techniques may put a smile on the patient's face, during examination, they each suffered from the same deficiency. Each personalization item had to be attached to the exterior of the stethoscope. Thus, each item could get knocked off and lost, could get in the way during exams, and none of the attached items allow for full sterilization of the stethoscope.

What is needed in the field is a way to personalize a stethoscope without incurring any of the drawbacks of the above, prior methods. The ideal personalization technique would not interfere with the normal operation of the stethoscope, would provide positive identification without the possibility of getting knocked off of the stethoscope, and would allow for full sterilization of the stethoscope.

SUMMARY OF THE INVENTION

A stethoscope that has been personalized, wherein the personalization is used to identify an owner of the stethoscope and to decorate the stethoscope. The personalization technique does not deter from the normal operation of the stethoscope, and cannot be knocked off of the stethoscope. The stethoscope comprises a diaphragm, a bell or housing that supports the diaphragm, and air filled sound tubes that connect the bell to an ear piece that fits inside the ears of an operator. The diaphragm is adapted to collect noises from a patient's body. The diaphragm includes a first surface on an exterior side of the stethoscope that is adapted to come into contact with the patient, and a second surface that is on an interior side of the stethoscope. The second surface includes a design that has been applied preferably using a reverse technique, so as to provide personalization that identifies the owner of the stethoscope. The design also serves to decorate the stethoscope and provide a brief distraction to an otherwise sterile and sometimes bleak environment. The design does not interfere with the diaphragm's ability to transmit sounds. The design is preferably hand painted on the second surface using a reverse application technique, wherein the foreground is applied first, the background is applied last, and images painted on the right, appear on the left. The diaphragm is preferably made of LEXAN. The design can also be a pre-manufactured sticker and a reproduction of a photograph.

It is an object of the present invention to provide for personalization of a stethoscope that does not interfere with the normal operation of the stethoscope.

It is another object of the present invention to provide a personalization technique that not only allows for decoration, but also provides for positive identification without the possibility of being separated from the stethoscope.

It is yet another object of the present invention to provide a personalization technique that allows for full sterilization of the stethoscope.

BRIEF DESCRIPTION OF THE DRAWINGS

The invention of the present application will be described in detail with reference to the accompanying drawing(s), given only by way of example, in which.

DETAILED DESCRIPTION OF THE INVENTION

Figure 1:
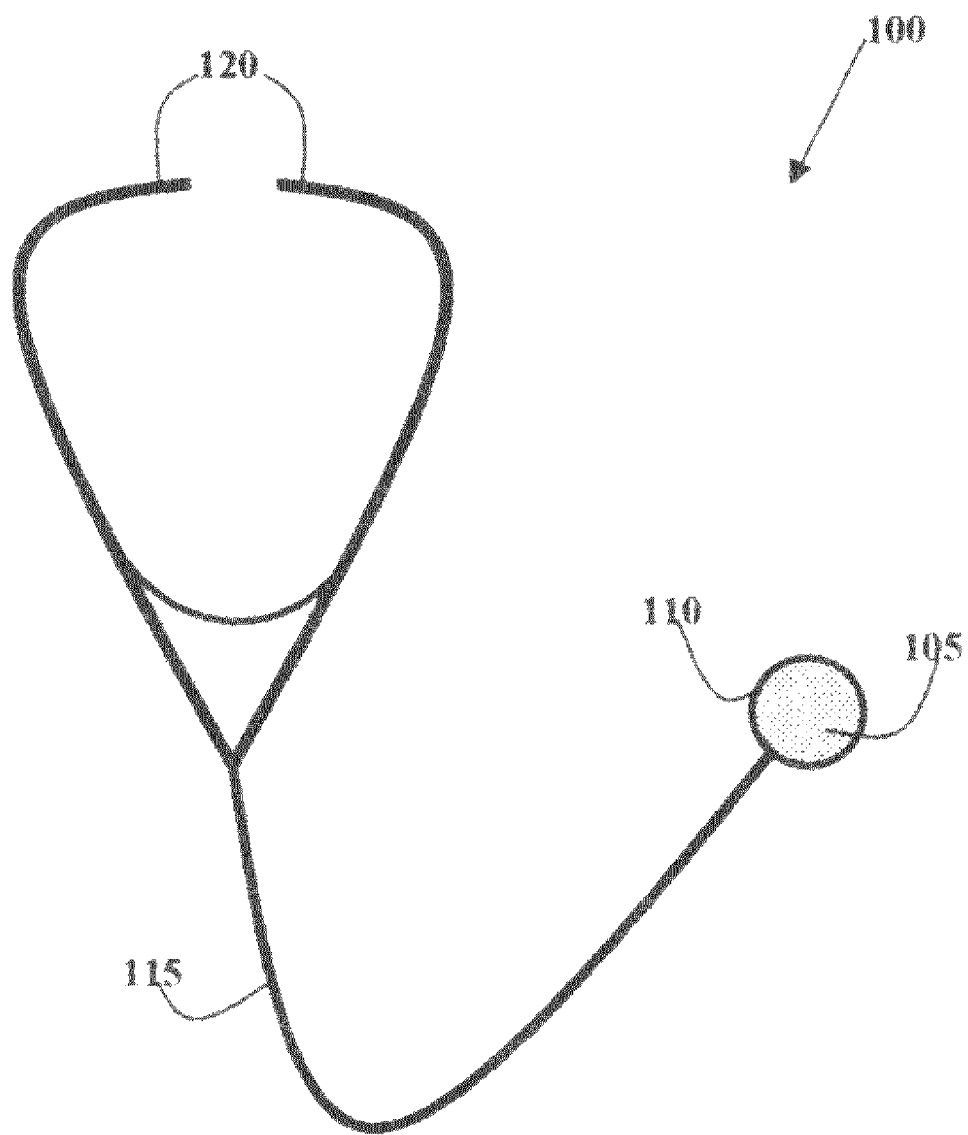
FIG. 1 shows a diaphragm in its operational position.

FIG. 1 shows a diaphragm 105 in its operational position within a stethoscope 100. The diaphragm 105 is held in place by a housing 110 that is mechanically connected to an air filled sound tube 115. The sound tube 115 splits into two separate tubes and connects to an ear piece 120. The ear piece 120 includes two endings that are adapted to fit inside the ears of an operator, such as a nurse or doctor. The diaphragm 105 appears to have a design on its outer surface. However, the design is actually applied to the interior surface of the diaphragm 105. The preferred method for applying the design, and thereby personalizing the stethoscope 100 is disclosed below.

Figure 2A:
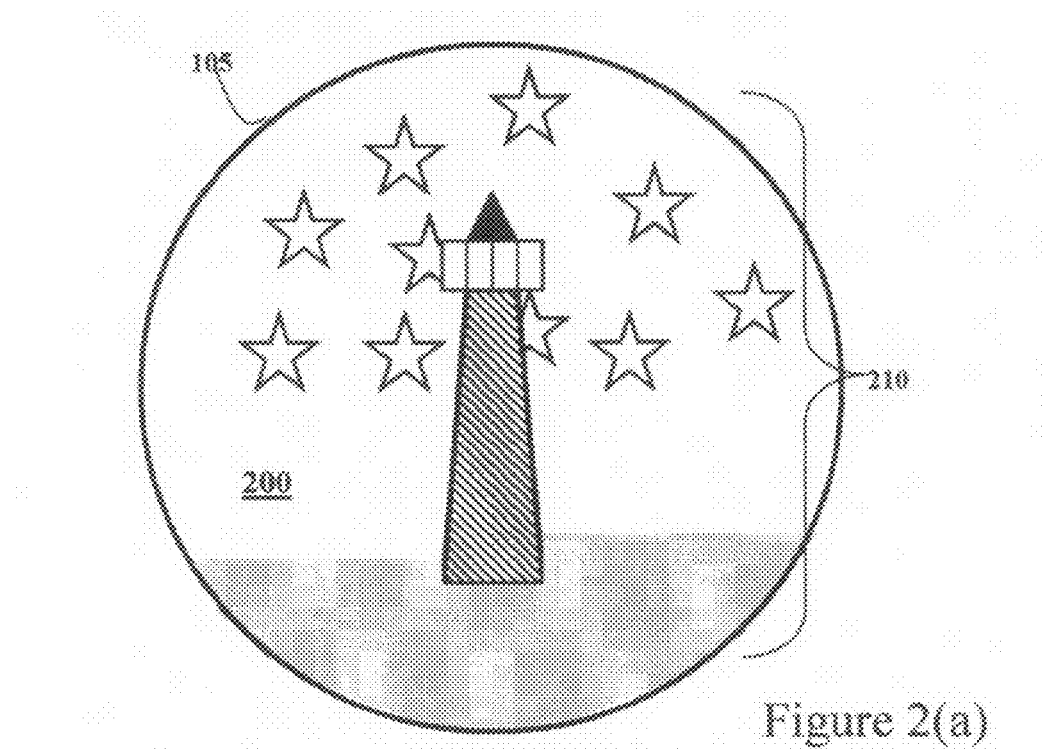
FIG. 2(a) shows the exterior surface of the diaphragm with a design that was applied using the present personalization technique.

FIG. 2(a) shows the exterior surface 200 of the diaphragm 105 with a design 210 that was applied using the present personalization technique. The design 210 includes a lighthouse in the foreground, a beach area in the mid-ground, and stars in the background. The present method advantageously decorates the interior side of the diaphragm 105, leaving the exterior side 200 without any additions to its surface. Thus the exterior side 200 of the diaphragm provides a clean, smooth surface for contacting the skin of a patient. The exterior side 200 of the diaphragm 105 can also be fully sterilized without damaging the design 210. Further, the owner is virtually guaranteed that after years of normal wear and tear, his identification and personalization design will not be knocked off or become separated from his stethoscope.

Figure 2B:
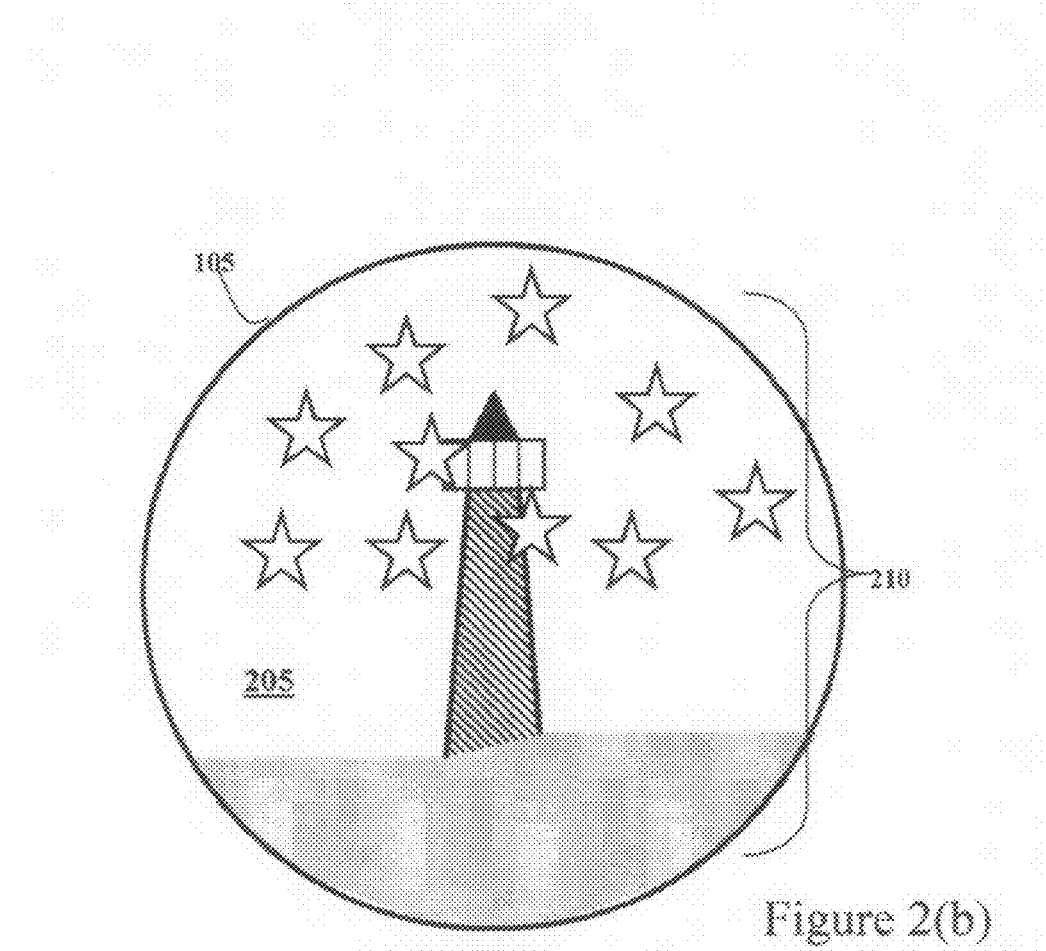
FIG. 2(b) shows the interior surface of the diaphragm with the design that was applied using the present personalization technique.

FIG. 2(b) shows the interior surface 205 of the diaphragm 105 with the design 210 that was applied using the present personalization technique. In the preferred embodiment, designs are hand painted on the interior surface 205 of the diaphragm 105 using a reverse application technique, wherein the foreground is applied first, any mid-ground second, and the background is applied last. In design 210, the stars are in the background, and thus are applied last. As seen in FIG. 2(b), the stars appear on top of lighthouse, because of the present reverse application technique. However, as seen in FIG. 2(a), when viewing the diaphragm 105 from the exterior side 200, the stars appear in the background, as they should. The present personalization technique will become more apparent with the below discussion of FIGS. 3-8.

Figure 3:
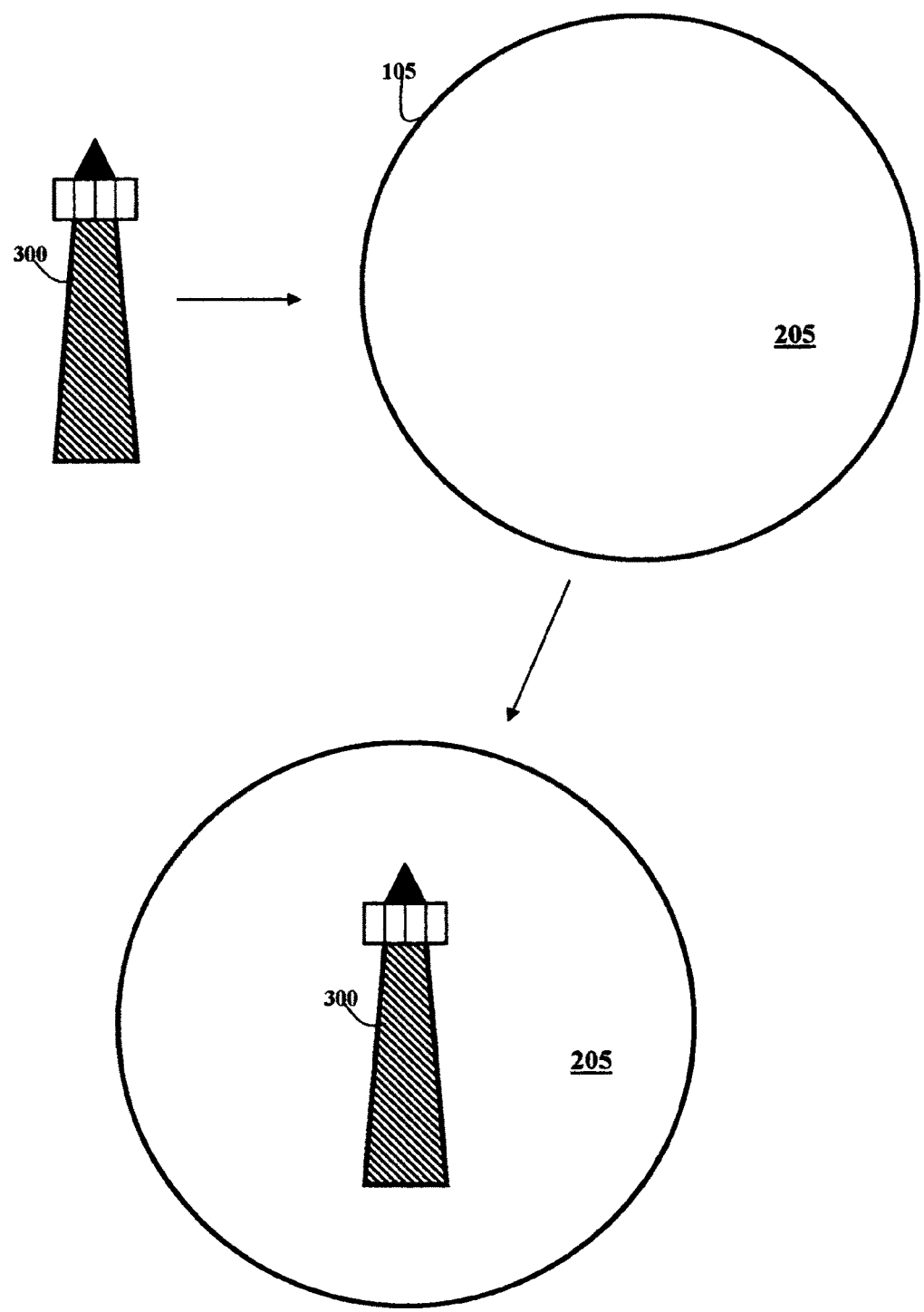
FIG. 3 shows the application of a foreground image to the interior surface of the diaphragm.

FIG. 3 shows the application of a foreground image, lighthouse 300, to the interior surface 205 of diaphragm 105. In the preferred embodiment, the diaphragm 105 is made from a material called Lexan. Lexan resin and Visualfx® resins are produced and sold by SABIC Innovative Plastics. Lexan polycarbonate resin is an amorphous engineering thermoplastic, characterized by outstanding mechanical, optical and thermal properties. The Lexan portfolio provides broad versatility including: scratch resistance, toughness, heat resistance, weatherability, biocompatibility, optical quality, and compliance with stringent FDA and USP requirements. Lexan is unmatched in performance features such as acoustic wave transfers. Lexan's increased strength allows diaphragms to be made thinner, thereby actually increasing wave transfer properties.

Figure 4:
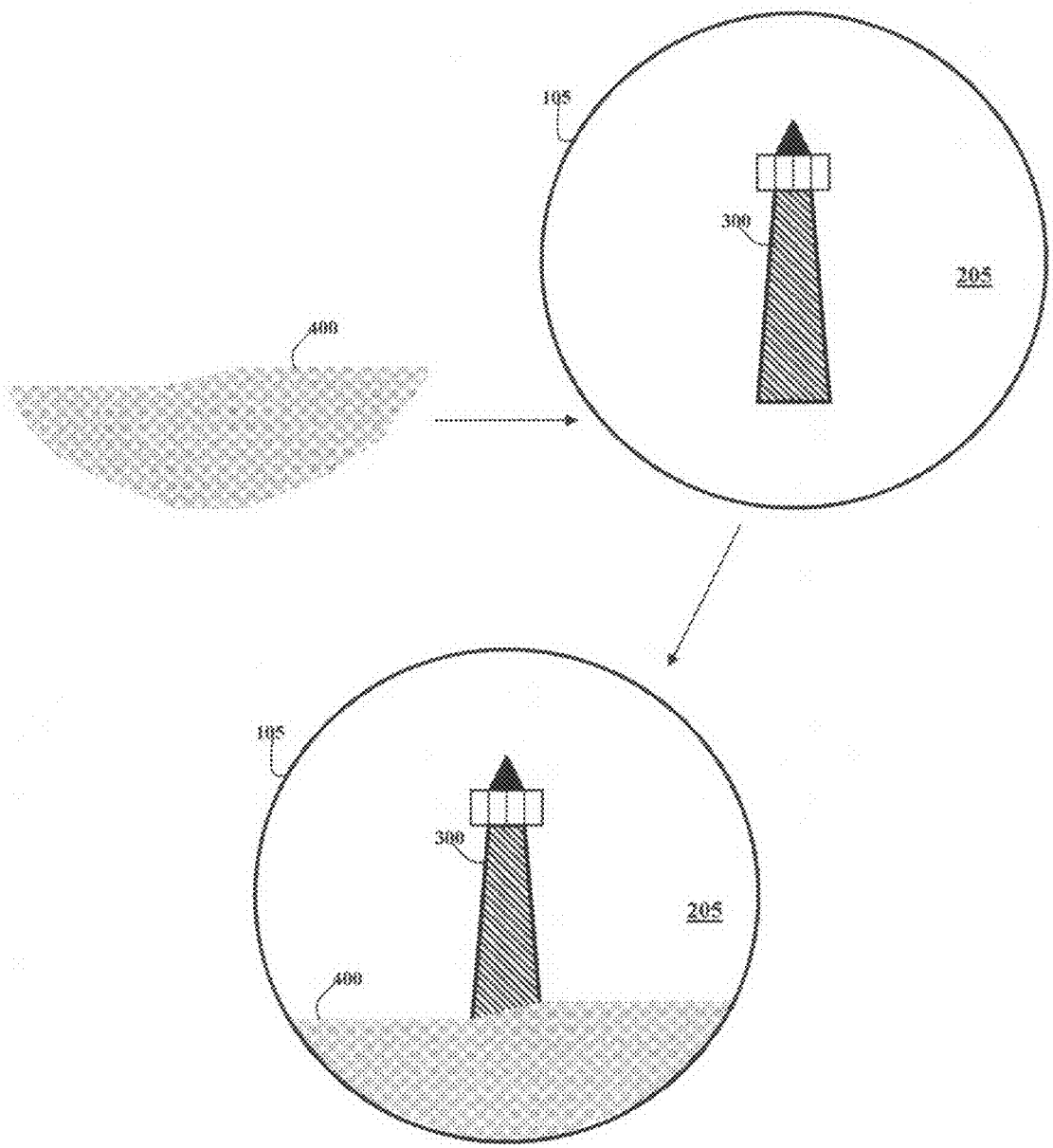
FIG. 4 shows the application of a mid-ground image to the interior surface.

FIG. 4 shows the application of a mid-ground image, beach 400, to the interior surface 205 of the diaphragm 105. The foreground image, or lighthouse 300, was previously applied to diaphragm 105. So, the mid-ground image, beach 400, goes "on top of" the lighthouse. In actuality, only of a small portion of the beach 400 overlaps the lighthouse 300. The amount of actual overlapping, or painting over, of layers, foreground, background, etc., of any specific design will depend on the design. In this case, only the upper portion of the beach 400 overlaps the bottom of the lighthouse 300.

Figure 5:
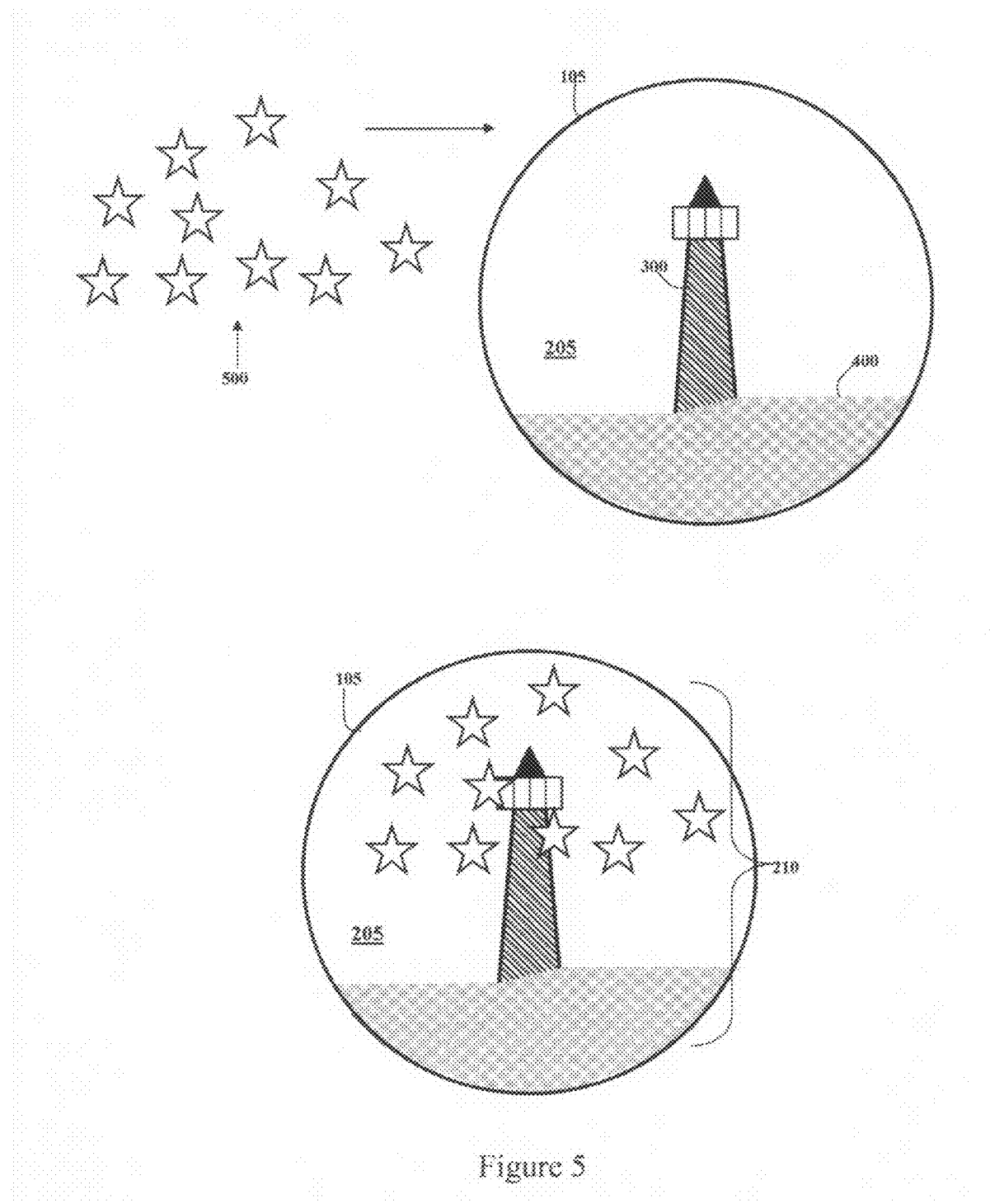
FIG. 5 shows the application of a background image to the interior surface.

FIG. 5 shows the application of a background image, stars 500, to the interior surface 205 of the diaphragm 105. The foreground and mid-ground images (lighthouse 300 and beach 400) were previously applied to diaphragm 105. So, the background image, stars 500, goes "on top of" the lighthouse and beach. In actuality, only two of the stars 400 overlap the lighthouse 300. Together, the lighthouse, beach and stars, make up the design 210, which the owner chose, in order to personalize his stethoscope. To see a view of the design 210 from the exterior side of the diaphragm 105, refer back to FIG. 2(a).

Figure 6:
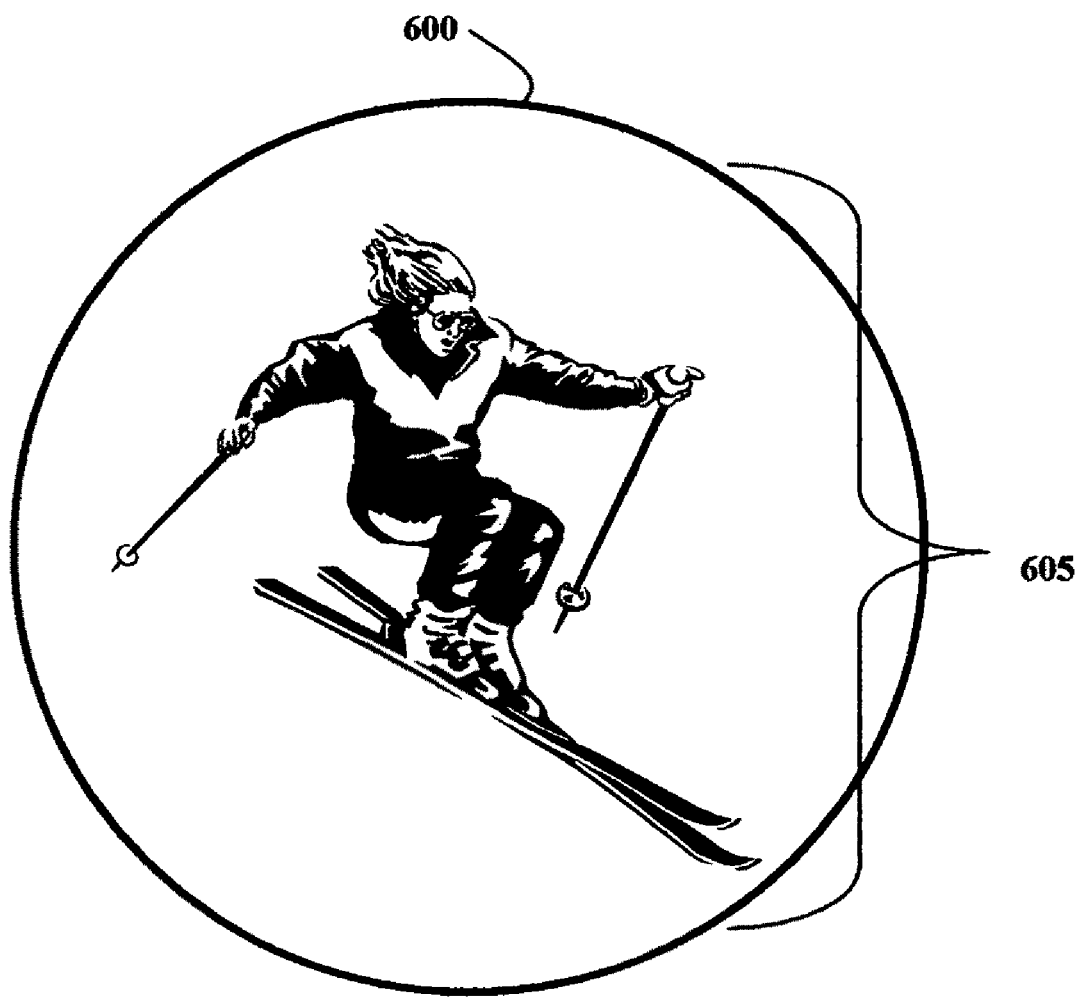
FIG. 6 shows a diaphragm with an alternative design that has been applied using the present personalization technique.

FIG. 6 shows a diaphragm 600 with an alternative design 605 that has been applied using the present personalization technique, wherein the design 605 is applied to the interior surface of the diaphragm 600. The design 605 can be a photograph, a reproduction of a photograph, such as a photograph that has been reproduced on a sticker. Other alternative designs include the use of decals, including rub-on decals, all well known types of paint and styles of painting, including spray-on and air-brushed, and stencils, and other well know tools for painters and artists.

Figure 7:
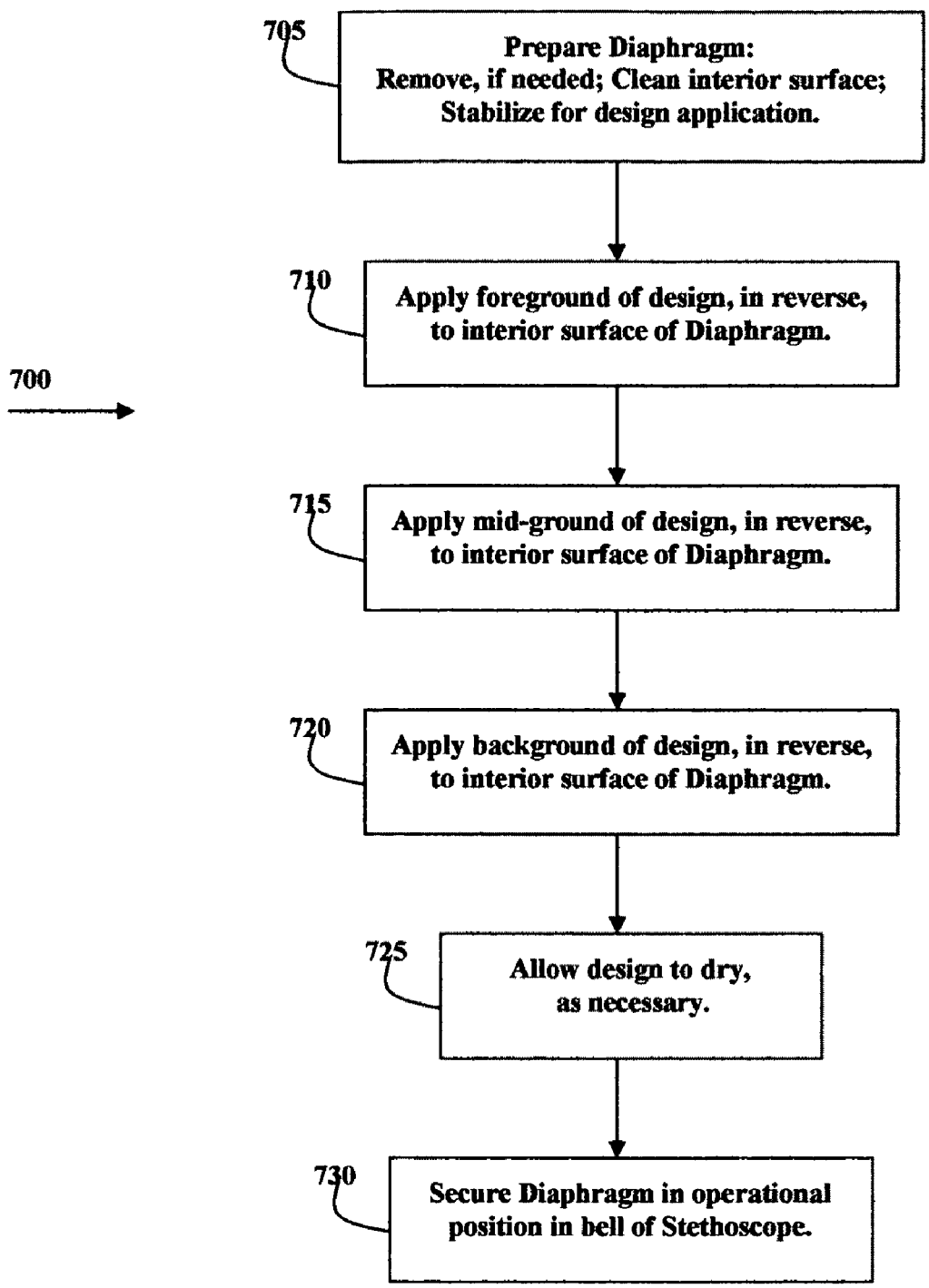
FIG. 7 is a flow chart showing exemplary steps of the preferred method.

FIG. 7 is a flow chart showing exemplary steps of the preferred method 700 of personalizing a stethoscope. In step 705, the diaphragm is prepared, meaning the interior surface is cleaned and the diaphragm is framed and clamped, or otherwise secured in place for painting. Prior to step 710, a design must be chosen. Preferably, the stethoscope owner will chose the design, or provide a design. In step 710, the foreground of the design is applied, in reverse, to the interior surface of the diaphragm. "In reverse" means that images painted on the left-half of the interior "canvas", as seen by the artist, will actually appear on the right-half of the diaphragm, when viewed by all others, i.e., from the exterior side. In step 715, the mid-ground of the design is applied, in reverse, to the interior surface of the diaphragm. Of course, if there is no mid-ground, then this step can be skipped. However, if there is more than one mid-ground, then this step is repeated. In step 720, the background of the design is applied, in reverse, to the interior surface of the diaphragm. Thus, each layer of the design is applied, one on top of the other, in reverse. Of course, appropriated drying time is allowed for each layer, step 725. After drying and any design specific finishing, the diaphragm is installed in its operational position, within the owner's stethoscope, step 730.

Figure 8:
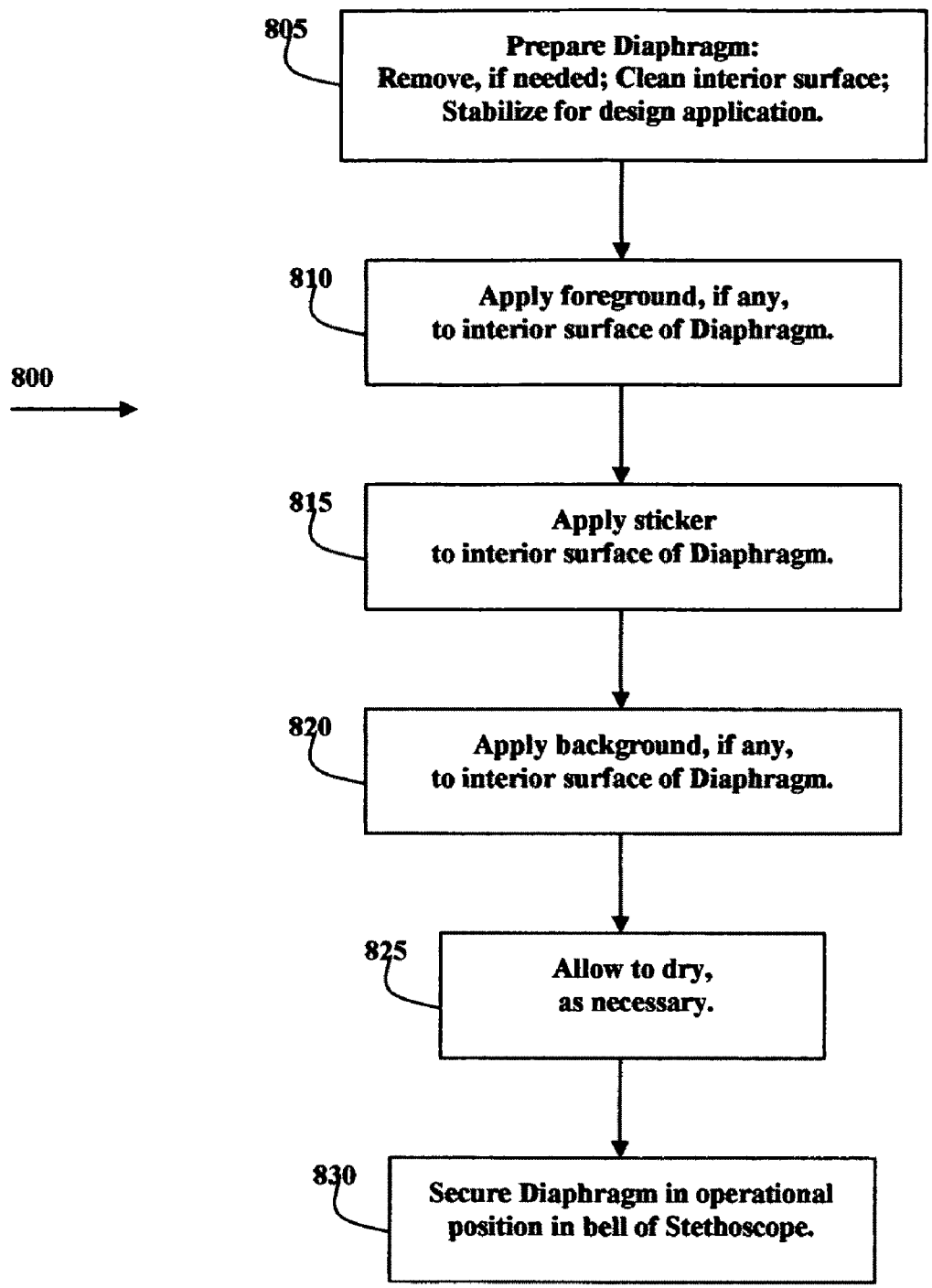
FIG. 8 is a flow chart showing exemplary steps in an alternative method.

FIG. 8 is a flow chart showing exemplary steps in an alternative method 800 for personalizing a stethoscope. In step 805, the diaphragm is prepared, meaning the interior surface is cleaned and the diaphragm is framed and clamped, or otherwise secured in place for design application. Prior to step 810, a design must be chosen. Preferably, the stethoscope owner will those the design, or provide a design. In step 810, the foreground, if there is one, is applied, in reverse, to the interior surface of the diaphragm. "In reverse" means that images applied to the left-half of the interior "canvas", as seen by the artist, will actually appear on the right-half of the diaphragm, when viewed by all others. In step 815, a pre-produced, one-sided sticker is applied to the interior surface of the diaphragm. If there is more than one sticker, or decal, then this step is repeated. In step 820, the background of the design, if any, is applied, in reverse, to the interior surface of the diaphragm. Of course, if the background is complete coverage in one color, then "in reverse" is not needed. Thus, the design in this alternative method allows for the use of stickers and decals. The pre-produced stickers can be complemented with a foreground and/or background, or can stand-alone. Appropriated drying time is allowed as needed for the design in step 825. After drying and any design specific finishing, the diaphragm is installed in its operational position, within the owner's stethoscope, step 830.

In another alternative method for personalizing a stethoscope, the diaphragm itself provides a decorative feature. Besides being shatter-resistant and virtually unbreakable LEXAN resin comes in virtually unlimited colors and hues, crystal-clear transparency or translucency to metal flake, speckle and light-diffused special effects.

The foregoing description of the specific embodiments will so fully reveal the general nature of the invention that others can, by applying current knowledge, readily modify and/or adapt for various applications such specific embodiments without departing from the generic concept. For example, the present method could be used on other equipment, such as on the interior surface of a drum or banjo, to provide ID and personalization. Therefore, such adaptations and modifications should and are intended to be comprehended within the meaning and range of equivalents of the disclosed embodiments. It is to be understood that the phraseology of terminology employed herein is for the purpose of description and not of limitation.

I claim:

1. A diaphragm that is adapted for use in a stethoscope, the diaphragm comprising:
   a first surface that is adapted for use on an exterior side of the stethoscope, wherein the first surface of the diaphragm is adapted to make contact with the skin of a patient so that sounds from the patient may be captured by the stethoscope; and,
   a second surface that is adapted for use on an interior side of the stethoscope, wherein a design has been applied to the second surface of the diaphragm so that the diaphragm is fully functional without the need of a membrane or lens to cover the design.

2. The diaphragm of claim 1, wherein the design is hand painted on the second surface, and wherein the diaphragm is interchangeable with another diaphragm.

3. The diaphragm of claim 1, wherein the design is painted on the second surface using a reverse application technique, wherein a foreground is applied first, a background is applied last, and images painted on a left side appear on a right side.

4. The diaphragm of claim 1, wherein the diaphragm is made of Lexan thereby making the diaphragm shatter-proof and impact resistant and thus making the diaphragm suitable for use by medical personnel in a combat environment.

5. The diaphragm of claim 1, wherein the design includes a pre-manufactured sticker.

6. The diaphragm of claim 1, wherein the design is a reproduction of a photograph.

7. A stethoscope that has been personalized wherein the personalization is used to identify an owner of the stethoscope and to decorate the stethoscope, wherein the personalization does not deter from the normal operation of the stethoscope, the stethoscope comprising:
   a diaphragm that is adapted to collect noises from a patient's body, wherein the diaphragm includes a first surface on an exterior side of the stethoscope that is adapted to come into contact with the patient; and, a second surface that is on an interior side of the stethoscope, wherein a design has been applied to the second surface so that the diaphragm is fully functional without the need of a membrane or lens to cover the design, the design providing the personalization that identifies the owner;
   a bell that houses and supports the diaphragm;
   an ear piece that is adapted to fit inside the ears of an operator; and,
   at least one sound tube that connects the bell to the ear piece, so that sounds captured by the diaphragm and bell are carried to the ears of the operator.

8. The stethoscope of claim 7, wherein the design is hand painted on the second surface, and wherein the diaphragm is interchangeable with another diaphragm.

9. The stethoscope of claim 7, wherein the design is painted on the second surface using a reverse application technique, wherein a foreground is applied first, a background is applied last, and images painted on a left side, appear on a right side.

10. The stethoscope of claim 7, wherein the diaphragm is made of Lexan thereby making the diaphragm shatter-proof and impact resistant and thus making the diaphragm suitable for use by medical personnel in a combat environment.

11. The stethoscope of claim 7, wherein the design includes a pre-manufactured sticker.

12. The stethoscope of claim 7, wherein the design is a reproduction of a photograph.

13. A method for personalizing a stethoscope, wherein personalization provides identification for an owner of the stethoscope and does not interfere in any way with standard daily sterilization of the stethoscope, the method comprising:
   applying a design to an interior side of a diaphragm, wherein the design was provided by, selected by, or otherwise identifies the owner;
   installing the diaphragm in the stethoscope so that the interior side is protected within an interior side of the stethoscope, and an exterior side of the diaphragm is adapted to make contact with a patient.

14. The method of claim 13, wherein the step of applying, comprises:
   applying a first layer of the design; and,
   applying a second layer of the design to the interior side of the diaphragm.

15. The method of claim 14, wherein both steps of applying the first and second layers of the design, comprise:
   painting the layers of the design on the diaphragm, in reverse.

16. The method of claim 15, wherein the first layer is a foreground of the design, and the second layer is a background of the design.

17. The method of claim 13, wherein the personalization provides the stethoscope with permanent identification of the owner, and wherein the design is applied using a reverse application technique.

18. The method of claim 13, wherein the diaphragm is made of Lexan thereby making the diaphragm shatter-proof and impact resistant and thus making the diaphragm suitable for use by medical personnel in a combat environment.

19. The method of claim 13, wherein the diaphragm is interchangeable with another diaphragm.

* * * * *